United States Patent
Al-Azmi

(12) 
(10) Patent No.: US 8,636,681 B1
(45) Date of Patent: Jan. 28, 2014

(54) SPLINT FOR THE ENTIRE LEG

(71) Applicant: Mohamad Saad Farhan Mutairan Al-Azmi, Salwa (KW)

(72) Inventor: Mohamad Saad Farhan Mutairan Al-Azmi, Salwa (KW)

( * ) Notice: Subject to any disclaimer, the term of this patent is extended or adjusted under 35 U.S.C. 154(b) by 0 days.

(21) Appl. No.: 13/904,865

(22) Filed: May 29, 2013

Related U.S. Application Data

(63) Continuation of application No. 13/652,448, filed on Oct. 15, 2012.

(51) Int. Cl.
*A61F 5/00* (2006.01)

(52) U.S. Cl.
USPC .......................................................... 602/23

(58) Field of Classification Search
USPC ........ 602/5, 19, 23–29, 60, 62; 128/882; 2/22
See application file for complete search history.

(56) References Cited

U.S. PATENT DOCUMENTS

| | | | |
|---|---|---|---|
| 1,184,868 A * | 5/1916 | Pierce | 2/22 |
| 1,916,789 A * | 7/1933 | Fordham | 602/5 |
| 2,753,864 A * | 7/1956 | Weidemann, Jr. | 602/23 |
| 4,513,740 A * | 4/1985 | Westlake | 602/62 |
| 4,580,555 A | 4/1986 | Coppess | |
| 4,607,628 A * | 8/1986 | Dashefsky | 602/26 |
| 5,230,697 A * | 7/1993 | Castillo et al. | 602/16 |
| 7,682,323 B2 | 3/2010 | DeToro et al. | |
| 7,892,195 B2 | 2/2011 | Grim et al. | |

* cited by examiner

*Primary Examiner* — Patricia Bianco
*Assistant Examiner* — Raymond E Harris
(74) *Attorney, Agent, or Firm* — Richard C. Litman

(57) ABSTRACT

The splint for the entire leg is a portable splint that is used to immobilize fractures that may occur to the leg of an accident victim. The splint includes two parts that are connectable when the splint is applied to the leg. An upper part functions to immobilize the femur and stabilize the hip. A lower part immobilizes the tibia and/or fibula and stabilizes the knee and foot. Straps are employed to secure the splint to the leg.

15 Claims, 4 Drawing Sheets

SPLINT FOR THE ENTIRE LEG

CROSS-REFERENCE TO RELATED APPLICATIONS

This is a continuation of my prior application Ser. No. 13/652,448, filed Oct. 15, 2012.

BACKGROUND OF THE INVENTION

1. Field of the Invention

The present invention generally relates to medical appliances, and particularly to a splint for the entire leg that immobilizes both the upper and lower leg.

2. Description of the Related Art

Accidents often occur wherein an entire leg of the victim is involved. Such an accident may require that the Emergency Medical Technician (EMT) or other first responder immobilize a fractured femur, tibia and/or fibula while also stabilizing the knee, hip and foot of the affected leg. Heretofore, portable splints are generally unable to accomplish all of the aforementioned procedures effectively and efficiently, thereby creating situations wherein the victim may be more seriously injured when moved to a waiting ambulance and from the ambulance to a hospital or the like. The emergency medical profession would eagerly embrace a portable splint that could easily perform the emergency procedures required. Thus, a splint for the entire leg solving the aforementioned problems is desired.

SUMMARY OF THE INVENTION

The splint for the entire leg is a portable splint that is used to immobilize fractures that may occur to the leg of an accident victim. The splint comprises two parts that are connectable when the splint is applied to the leg. An upper part functions to immobilize the femur and stabilize the hip. A lower part immobilizes the tibia and/or fibula and stabilizes the knee and foot. Straps are employed to secure the splint to the leg.

Accordingly, the invention presents a portable splint that is versatile and can be quickly and easily applied to the leg of an accident victim. The splint is constructed from strong, lightweight materials and is padded for comfort. The invention provides for improved elements thereof in an arrangement for the purposes described that are inexpensive, dependable and fully effective in accomplishing their intended purposes.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENT

Figure 1:
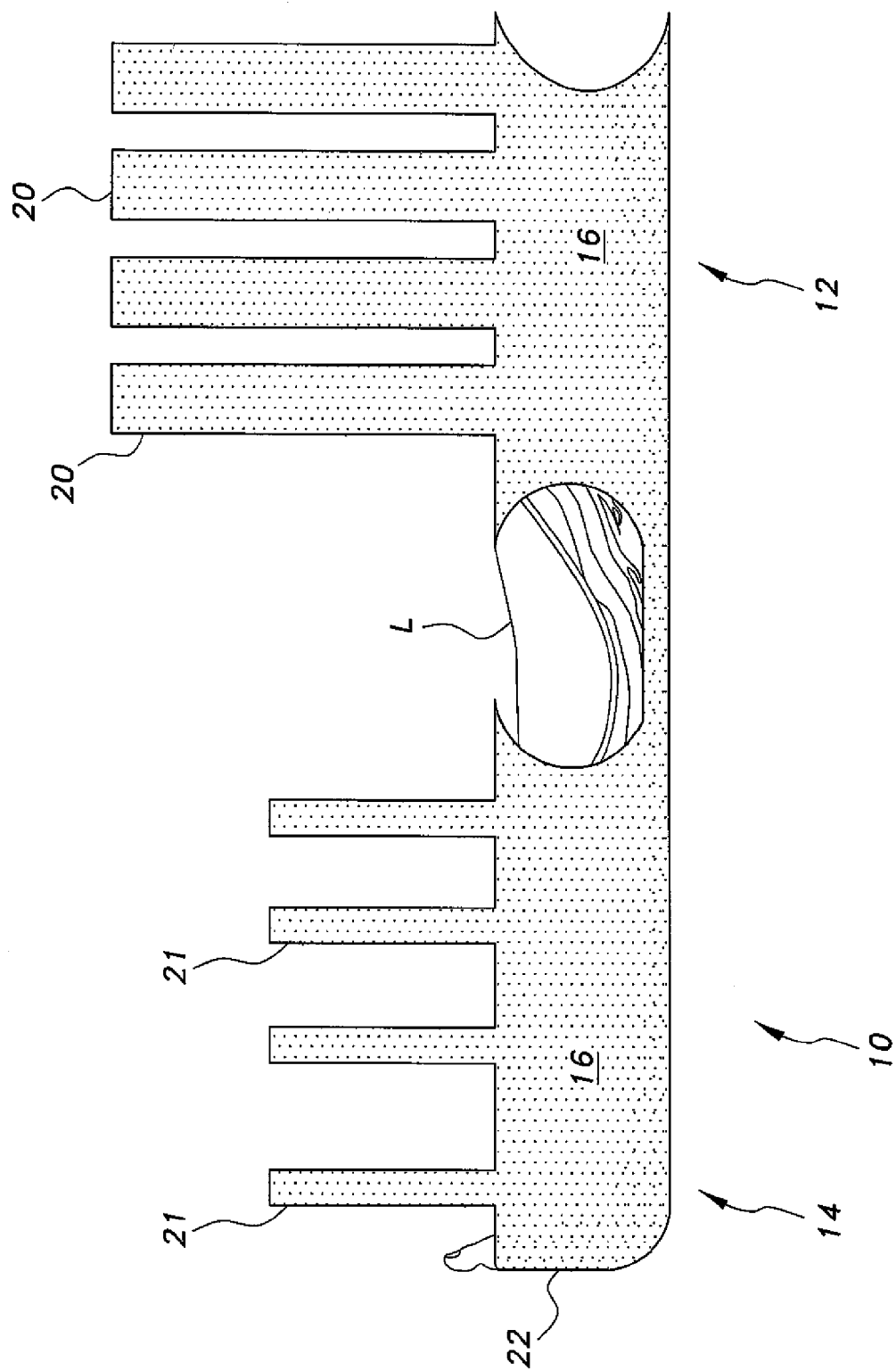
FIG. 1 is a partial environmental side view of a splint for the entire leg according to the present invention, shown with a leg in the splint and before securing the straps.
Figure 2:
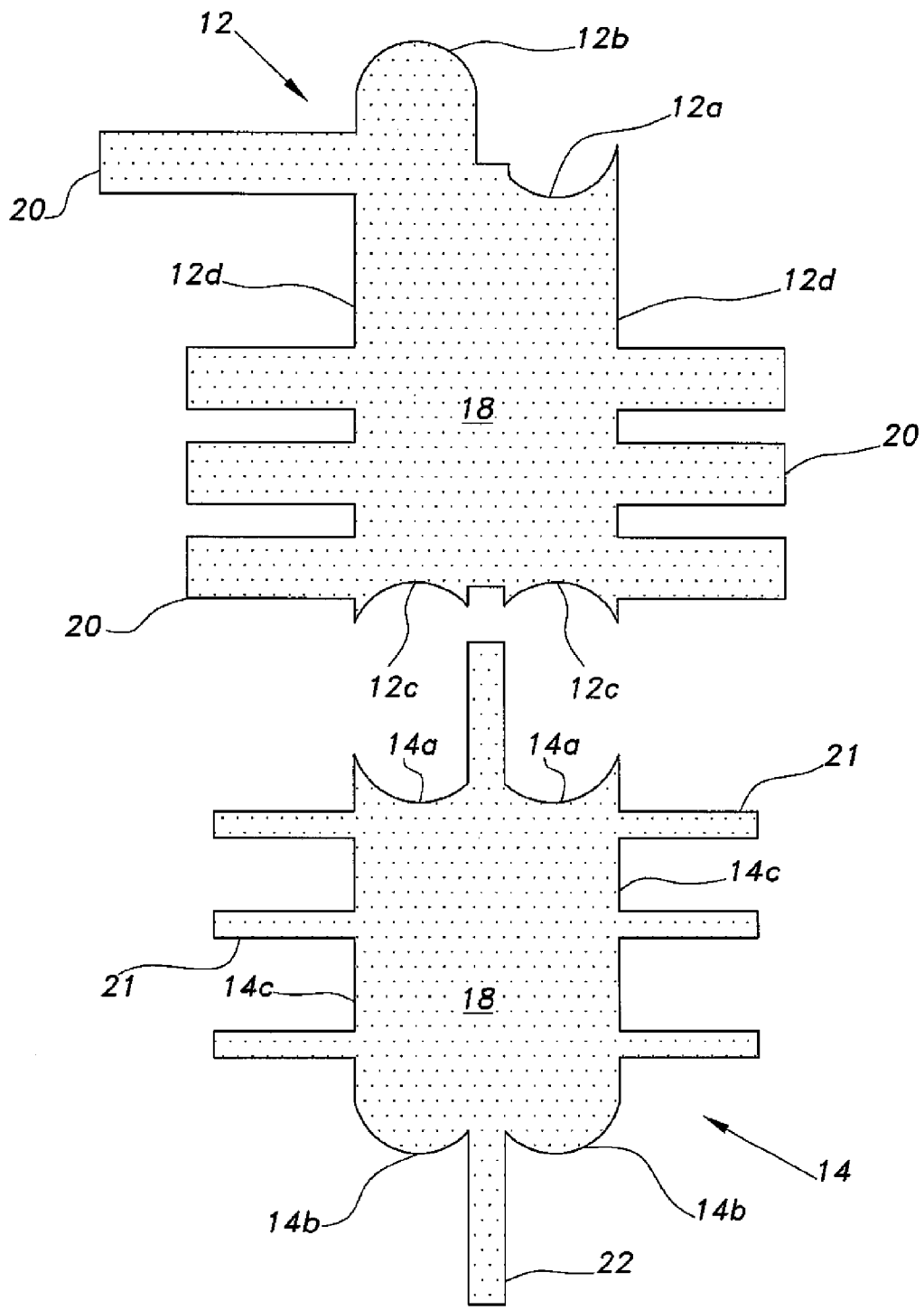
FIG. 2 is an exploded front view of the splint of FIG. 1.
Figure 3:
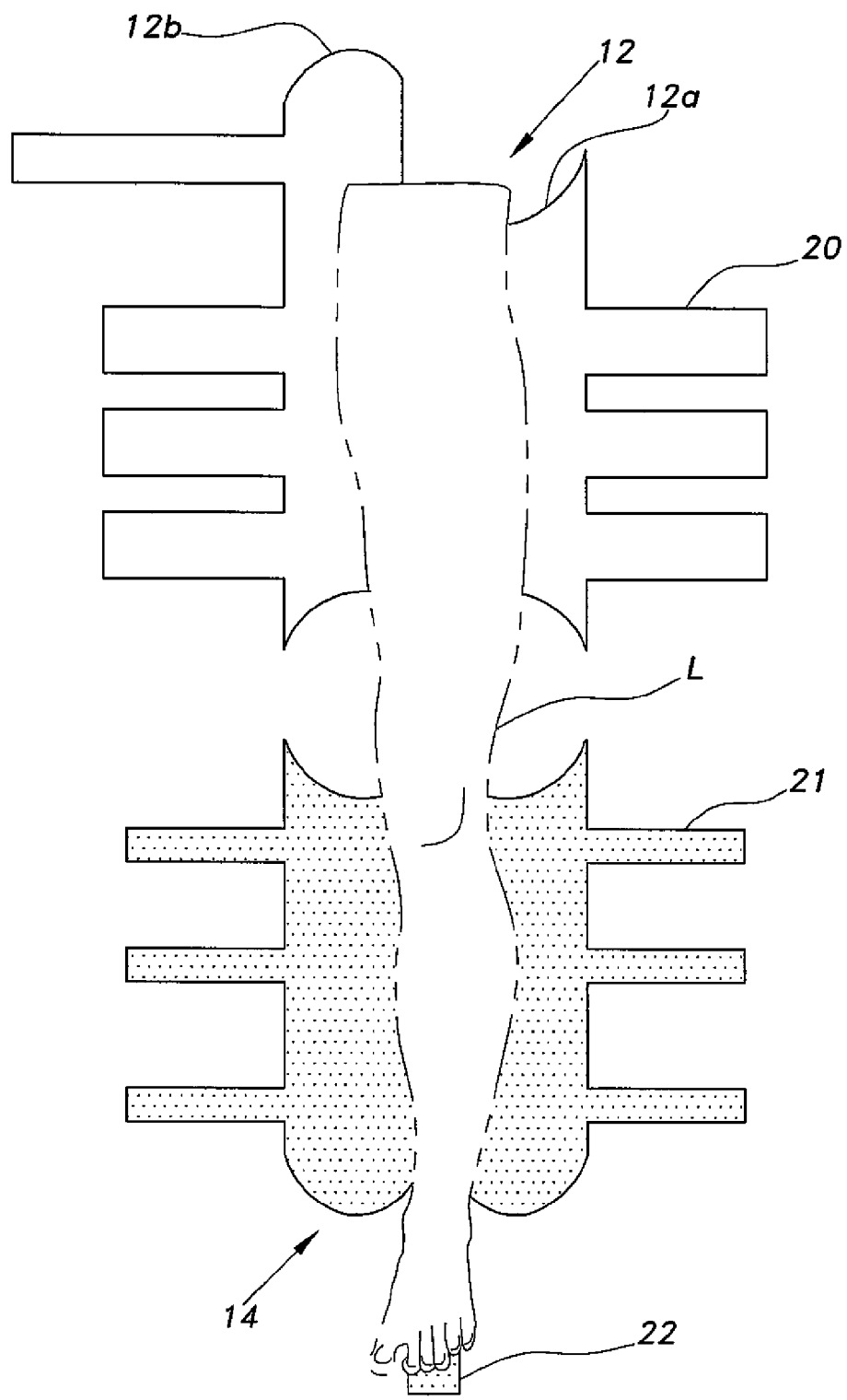
FIG. 3 is an environmental front view of the splint of FIG. 1, showing the splint being positioned on the leg.

With reference to FIGS. 1-4, the splint for the entire leg, generally indicated at 10, includes an upper member 12 and a lower member 14 adapted to encase the entire leg L of a victim involved in an accident. Both members comprise respective lateral and medial surfaces 16, 18 for covering the outer and inner aspects of the leg, respectively. Both surfaces are covered with a smooth layer of sponge material covered with a thin sheet of plastic. The sponge layer enhances comfort and the plastic tissue covering allows the splint to be cleaned by wiping the surface with a soft damp cloth. The upper member 12 is provided with a contoured upper edge that permits the upper portion to fit around the hip area of the victim and stabilize the hip joint. The upper edge includes a concave portion 12a and a convex portion 12b. The portions are spaced apart a distance for reasons explained below. The convex portion 12b extends upward a distance above concave portion 12a. The lower edge of upper member 12 comprises spaced adjacent portions 12c contoured in concave configurations to provide an opening to expose the knee. A plurality of straps 20 extend from the lateral edges 12d of the upper member 12. Straps 20 are utilized to secure the upper member 12 to the upper part of the leg L, e.g., with mating hook and loop fasteners, thereby immobilizing the femur and stabilizing the hip joint.

The lower member 14 is provided with an upper edge having spaced adjacent portions 14a that are contoured in concave configurations to provide an opening to expose the knee. The lower edge of lower member 14 is formed with spaced, adjacent convex portions 14b to permit the splint 10 to fit above the foot and around the ankle. Straps 21 for securing the splint to the lower leg (e.g., with mating hook and loop fasteners) extend from the lateral edges 14c of the lower member 14. Due to the usual size difference between the upper leg and the lower leg, the straps 20 may be wider and longer than straps 21. The straps may be fastened in any conventional manner (hook and loop, buckles, buttons, etc.). A support 22 is positioned between convex portions 14b and extends downward from the lower edge of the lower member. Support 22 is fabricated from a semi-rigid bendable material, e.g., plastic and is employed to be positioned under the victim's foot for stabilization thereof when the splint 10 is applied.

Figure 4:
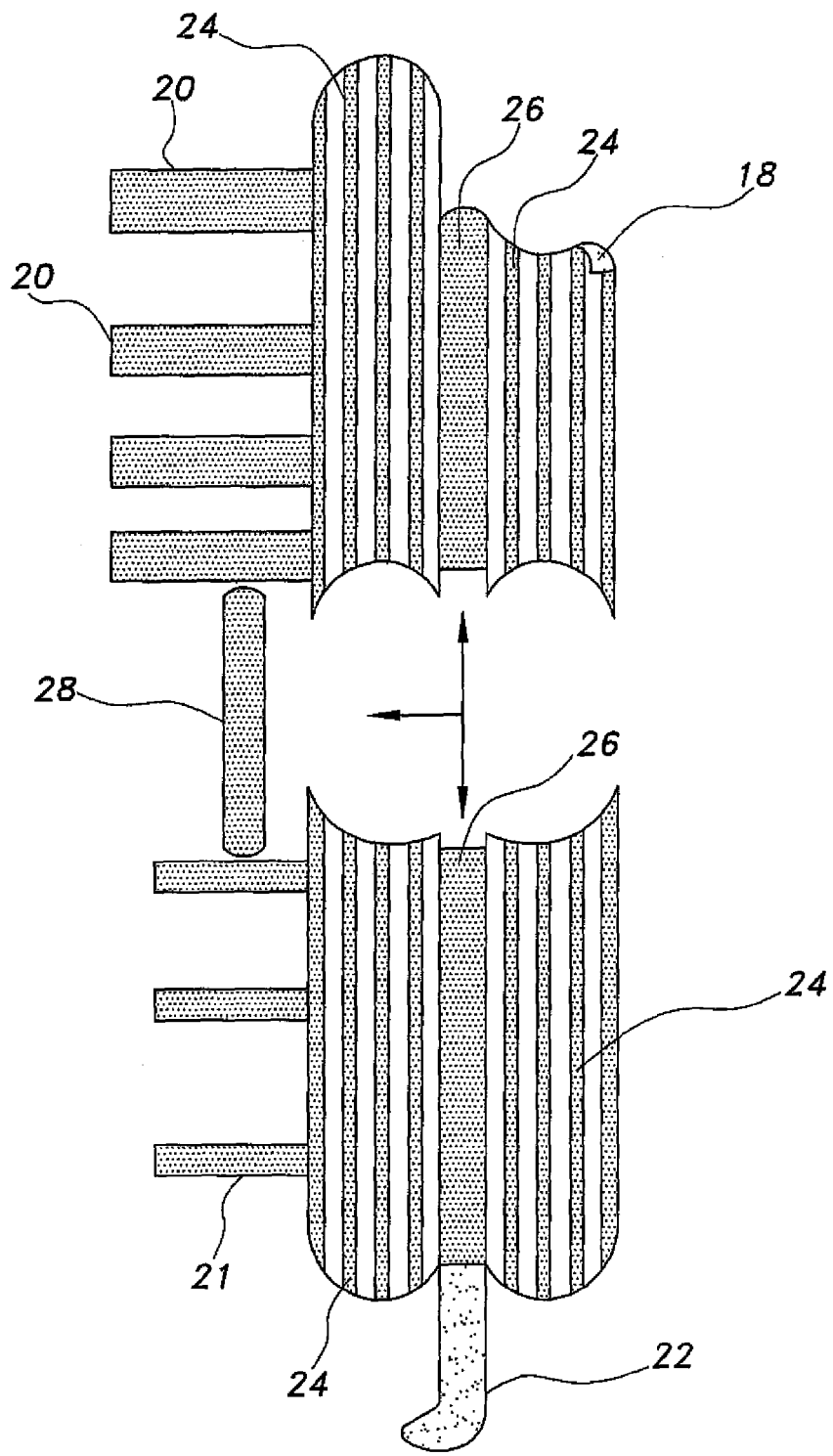
FIG. 4 is an exploded front view in section of the splint of FIG. 1, showing the inner construction of the splint.

As best seen in FIG. 4, the inner and outer surfaces of the splint 10 encapsulate a plurality of elongate, rigid ribs or slats 24. The slats 24 are arranged in a parallel array and are fabricated from a material that is stiff enough to keep the leg immobilized. The slats 24 may be maintained in position by enclosing the slats 24 in pockets, and the slats 24 may be separated by alternating strips of sponge rubber or foam rubber for comfort. Although wood is the preferred material, it is recognized that a plastic or metal material may also prove sufficient. A flexible fabric section 26, e.g., a strap of nylon webbing, is provided in the space between the contoured portions of the upper and lower splint members 12, 14. A connection member 28, e.g., a strap of nylon webbing, is adapted for attachment to the fabric sections 26 to connect the upper and lower members 12, 14 when the splint 10 is applied to the leg L. The connection member 28 is fabricated from a semi-rigid material and is covered with the same material used on the inner and outer surfaces of the splint. The connection member 28 also functions to provide stabilizing support for the knee.

It is to be understood that the present invention is not limited to the embodiments described above, but encompasses any and all embodiments within the scope of the following claims.

I claim:

1. A splint for the entire leg, comprising:
   an upper member having a medial portion, a lateral portion, a flexible portion connecting the medial portion with the lateral portion, an upper edge, a lower edge and lateral edges, the upper edge of the lateral portion being convex and the upper edge of the medial portion being concave, the lower edge of both the medial and the lateral portions being concave;
   a lower member having a medial portion, a lateral portion, a flexible portion connecting the medial portion with the lateral portion, an upper edge, a lower edge and lateral edges, the upper edge of both the lateral and medial portions being concave, and the lower edge of both the lateral and medial portions being convex;
   a first plurality of securing straps attached to the lateral edges of the upper member; and
   a second plurality of securing straps attached to the lateral edges of the lower member.

2. The splint according to claim 1, further including a foot support member extending downward from the lower edge of said lower member.

3. The splint according to claim 2, wherein said foot support member is fabricated from a semi-rigid bendable material.

4. The splint according to claim 1, wherein each said strap in the first plurality of securing straps is wider and longer than each said strap in the second plurality of securing straps.

5. The splint according to claim 1, further including a connecting member attachable to the flexible portions of said upper member and said lower member to connect said upper member to said lower member.

6. The splint according to claim 1, wherein said upper member and said lower member encapsulate a plurality of elongate rigid slats therein.

7. The splint according to claim 1, wherein the lateral and the medial portions of said upper and lower members are fabricated of a smooth layer of sponge material covered with a thin sheet of plastic.

8. A splint for the entire leg, comprising:
   an upper member having a medial portion, a lateral portion, a flexible portion connecting the medial portion with the lateral portion, an upper edge, a lower edge and lateral edges, the upper edge of the lateral portion being convex and the upper edge of the medial portion being concave, the lower edge of both the medial and the lateral portions being concave;
   a lower member having a medial portion, a lateral portion, a flexible portion connecting the medial portion with the lateral portion, an upper edge, a lower edge and lateral edges, the upper edge of both the lateral and medial portions being concave, and the lower edge of both the lateral and medial portions being convex;
   a connecting member attachable to the flexible portions of said upper member and said lower member to connect said upper member to said lower member
   a first plurality of securing straps attached to the lateral edges of the upper member;
   a second plurality of securing straps attached to the lateral edges of the lower member; and
   a foot support member extending downward from the lower edge of the lower member.

9. The splint according to claim 8, wherein each said strap in the first plurality of securing straps is wider and longer than each said strap in the second plurality of securing straps.

10. The splint according to claim 8, wherein said upper member and said lower member encapsulate a plurality of elongate rigid slats therein.

11. The splint according to claim 8, wherein the lateral and the medial portions of said upper and lower members are fabricated of a smooth layer of sponge material covered with a thin sheet of plastic.

12. The splint according to claim 8, wherein said foot support member is fabricated from a semi-rigid bendable material.

13. A splint support for the entire leg, comprising:
   an upper member having a medial portion, a lateral portion, a flexible portion connecting the medial portion with the lateral portion, an upper edge, a lower edge and lateral edges, the upper edge of the lateral portion being convex and the upper edge of the medial portion being concave, the lower edge of both the medial and the lateral portions being concave;
   a lower member having a medial portion, a lateral portion, a flexible portion connecting the medial portion with the lateral portion, an upper edge, a lower edge and lateral edges, the upper edge of both the lateral and medial portions being concave, and the lower edge of both the lateral and medial portions being convex;
   a connecting member attachable to the flexible portions of said upper member and said lower member to connect said upper member to said lower member
   a plurality of elongate rigid slats encapsulated within the upper member and the lower member;
   a first plurality of securing straps attached to the lateral edges of the upper member;
   a second plurality of securing straps attached to the lateral edges of the lower member; and
   a foot support member extending downward from the lower edge of the lower member, the foot support member being fabricated from a semi-rigid bendable material.

14. The splint according to claim 13, wherein each said strap in the first plurality of securing straps is wider and longer than each said strap in the second plurality of securing straps.

15. The splint according to claim 14, wherein the lateral and the medial portions of said upper and lower members are fabricated of a smooth layer of sponge material covered with a thin sheet of plastic.

* * * * *